(12) United States Patent
Arnaud et al.

(10) Patent No.: US 6,843,982 B1
(45) Date of Patent: Jan. 18, 2005

(54) ANHYDROUS COSMETIC OR DERMATOLOGICAL COMPOSITION CONTAINING THE COMBINATION OF A SILICONE OIL AND A WAX MADE FROM AN ETHYLENE HOMOPOLYMER OR COPOLYMER

(75) Inventors: Pascal Arnaud, Creteil (FR); Myriam Mellul, L'Hay les Roses (FR)

(73) Assignee: L'Oreal, Paris (FR)

( * ) Notice: Subject to any disclaimer, the term of this patent is extended or adjusted under 35 U.S.C. 154(b) by 56 days.

(21) Appl. No.: 09/049,927

(22) Filed: Mar. 30, 1998

Related U.S. Application Data

(63) Continuation of application No. 08/672,082, filed on Jun. 26, 1996, now Pat. No. 5,750,095, which is a continuation of application No. 08/377,382, filed on Jan. 25, 1995, now Pat. No. 5,556,613.

(30) Foreign Application Priority Data

Jan. 26, 1994  (FR) ............................................. 94 00843

(51) Int. Cl.$^7$ ......................... A61K 7/02; A61K 7/027; A61K 7/031
(52) U.S. Cl. ............................ 424/64; 424/59; 424/63; 424/70.12; 424/401; 514/844; 514/845
(58) Field of Search ............................. 424/59, 63, 64, 424/401, 70.12; 514/844, 845

(56) References Cited

U.S. PATENT DOCUMENTS

| | | |
|---|---|---|
| 2,627,938 A | 2/1953 | Frohmader et al. |
| 2,628,187 A | 2/1953 | Frohmader et al. |
| 2,992,201 A | 7/1961 | Gober, Jr. |
| 3,196,079 A | 7/1965 | Blaustein |
| 3,215,599 A | 11/1965 | Thau et al. |
| 3,645,904 A | 2/1972 | Beach |
| 3,919,357 A | 11/1975 | Keegan et al. |
| 3,970,577 A | 7/1976 | Glück et al. |
| 4,011,251 A | 3/1977 | Tjurin et al. |
| 4,022,730 A | 5/1977 | Lewis et al. |
| 4,164,563 A | 8/1979 | Chang |
| 4,199,599 A | 4/1980 | Klein |
| 4,200,561 A | 4/1980 | Chang |
| 4,246,257 A | 1/1981 | Elliott et al. |
| 4,518,509 A | 5/1985 | Newberry |
| 4,574,082 A | 3/1986 | Tietjen et al. |
| 4,698,359 A | 10/1987 | Niederer et al. |
| 4,699,780 A | 10/1987 | Jennings et al. |
| 4,834,972 A | 5/1989 | Chang |
| 4,874,868 A | 10/1989 | Bolich, Jr. |
| 4,919,934 A | 4/1990 | Deckner et al. |
| 4,935,228 A | 6/1990 | Finkenauer et al. |
| 4,990,561 A | 2/1991 | Yoshioka |
| 5,002,762 A | 3/1991 | Bolich, Jr. Raymond E. |
| 5,039,518 A | 8/1991 | Barone et al. |
| 5,080,889 A | 1/1992 | Katada et al. |
| 5,085,855 A | 2/1992 | Shore |

(List continued on next page.)

FOREIGN PATENT DOCUMENTS

| | | |
|---|---|---|
| DE | 1299788 | 11/1960 |
| DE | 1519376 | 3/1965 |
| DE | 1519376 | 6/1973 |
| DE | 217530 | 1/1985 |
| EP | 0 005 922 A1 | 12/1979 |
| EP | 17119 | 10/1980 |
| EP | 0103995 B1 | 3/1984 |
| EP | 0 133 963 B1 | 3/1985 |
| EP | 0 133 964 B1 | 3/1985 |
| EP | 0 270 339 B1 | 6/1988 |
| EP | 0 370 470 B1 | 5/1990 |
| EP | 370470 | 5/1990 |
| EP | 0 438 598 A1 | 7/1991 |

(List continued on next page.)

OTHER PUBLICATIONS

U.S. patent 5,039,518 Test Results (English Translation, French Original).

(List continued on next page.)

Primary Examiner—Evelyn Mei Huang
(74) Attorney, Agent, or Firm—Oblon, Spivak, McClelland, Maier & Neustadt, P.C.

(57) ABSTRACT

A silicone oil-based anhydrous cosmetic or dermatological anhydrous composition having a homogeneous fatty phase wherein said fatty phase contains a silicone oil having the formula $$\text{CH}_3-\underset{\underset{R}{|}}{\overset{\overset{R}{|}}{\text{Si}}}-\text{O}-\left[\underset{\underset{\phi}{|}}{\overset{\overset{\phi}{|}}{\text{Si}}}-\text{O}\right]_n\left[\underset{\underset{O}{|}}{\overset{\overset{\phi}{|}}{\text{Si}}}-\text{O}\right]_m-\underset{\underset{R}{|}}{\overset{\overset{R}{|}}{\text{Si}}}-\text{CH}_3 \quad (I)$$

(with pendant $\text{CH}_3-\underset{\underset{\text{CH}_3}{|}}{\overset{\overset{\text{CH}_3}{|}}{\text{Si}}}-\text{CH}_3$ group)

wherein
R represents alkyl having 1 to 30 carbon atoms, aryl or aralkyl,
n represents a whole number between 0 and 100, and
m represents a whole number between 0 and 100, provided that the sum of n + m is between 1 and 100; and
(ii) a wax in an amount ranging from 3 to 50 percent by weight based on the total weight of said fatty phase having a melting point between 50 and 135° C., comprising at least polymer having a molecular weight between 200 and 1,500 and selected from ethylene homopolymers and copolymers, and a monomer having the formula:

$$\text{CH}_2=\text{CH}-\text{R}' \quad (II)$$

wherein
R' represents alkyl having 1 to 30 carbon atoms, aryl or aralkyl.

90 Claims, No Drawings

U.S. PATENT DOCUMENTS

| | | |
|---|---|---|
| 5,102,656 A | 4/1992 | Kasat |
| 5,122,519 A | 6/1992 | Ritter |
| 5,143,723 A | 9/1992 | Calvo et al. |
| 5,213,716 A | 5/1993 | Patel et al. |
| 5,302,380 A | 4/1994 | Castrogiovanni et al. |
| 5,356,627 A | 10/1994 | Da Cunha et al. |
| 5,358,719 A | 10/1994 | Mellul et al. |
| 5,427,790 A | 6/1995 | Frische et al. |
| 5,648,066 A | 7/1997 | Stepniewski |
| 5,688,831 A | 11/1997 | El-Nokaly et al. |

FOREIGN PATENT DOCUMENTS

| | | |
|---|---|---|
| EP | 0 445 342 B1 | 9/1991 |
| EP | 0 451 786 A2 | 10/1991 |
| EP | 0 497 144 A1 | 8/1992 |
| EP | 497144 | 8/1992 |
| EP | 0 519 727 A1 | 12/1992 |
| EP | 0 544 330 A2 | 6/1993 |
| EP | 544330 | 6/1993 |
| EP | 547897 | 6/1993 |
| EP | 0 547 897 A2 | 6/1993 |
| EP | 0 681 830 A1 | 11/1995 |
| GB | 1060620 | 3/1967 |
| GB | 1140536 | 1/1969 |
| GB | 1161447 | 8/1969 |
| GB | 1300223 | 12/1972 |
| GB | 1341855 | 12/1973 |
| GB | 1370699 | 10/1974 |
| GB | 1373937 | 11/1974 |
| GB | 1537820 | 1/1979 |
| GB | 1557285 | 12/1979 |
| GB | 2 028 131 A | 3/1980 |
| GB | 1579934 | 11/1980 |
| JP | 50151940 | 12/1975 |
| JP | 57031611 | 2/1982 |
| JP | 57131272 | 8/1982 |
| JP | 58-15904 | 1/1983 |
| JP | 58015904 | 1/1983 |
| JP | 60248604 | 5/1984 |
| JP | 60-181011 | 9/1985 |
| JP | 60219274 | 11/1985 |
| JP | 60255714 | 12/1985 |
| JP | 85255714 | 12/1985 |
| JP | 61073750 | 4/1986 |
| JP | 62027078 | 2/1987 |
| JP | 62169714 | 7/1987 |
| JP | 63183516 | 7/1987 |
| JP | 01061409 | 8/1987 |
| JP | S62-238212 | 10/1987 |
| JP | 01139522 | 11/1987 |
| JP | 01149707 | 12/1987 |
| JP | 01006049 | 1/1989 |
| JP | 02184614 | 1/1989 |
| JP | 01061409 | 3/1989 |
| JP | 01079104 | 3/1989 |
| JP | S64-79106 | 3/1989 |
| JP | 01113311 | 5/1989 |
| JP | 01143812 | 6/1989 |
| JP | 03093708 | 9/1989 |
| JP | H1-283209 | 11/1989 |
| JP | 01283209 | 11/1989 |
| JP | 04091010 | 8/1990 |
| JP | 04142305 | 10/1990 |
| JP | H3-176411 | 7/1991 |
| JP | 03-176411 | 7/1991 |
| JP | 04026613 | 1/1992 |
| JP | H4-57894 | 2/1992 |
| JP | 04041536 | 2/1992 |
| JP | 05262618 | 3/1992 |
| JP | 5262619 | 3/1992 |
| JP | 04-342513 | 11/1992 |
| JP | 04342513 | 11/1992 |
| JP | 06299190 | 4/1993 |
| JP | H5-178865 | 7/1993 |
| JP | 07089844 | 9/1993 |
| JP | 07179819 | 11/1993 |
| JP | 07149613 | 12/1993 |
| JP | 07179718 | 12/1993 |
| JP | 08129338 | 9/1994 |
| JP | 08133926 | 11/1994 |
| JP | H7-48228 | 2/1995 |
| JP | 07-048228 | 2/1995 |
| JP | 07233029 | 9/1995 |
| JP | 08-026934 | 1/1996 |
| JP | 08 59428 | 3/1996 |
| JP | 08 73744 | 3/1996 |
| JP | 09-151109 | 6/1997 |
| NL | 6817346 | 6/1969 |
| PL | 126397 | 9/1985 |
| WO | WO 92/09263 | 6/1992 |
| WO | WO 92/19215 | 11/1992 |
| WO | WO 9504517 | 2/1995 |
| WO | WO 9509598 | 4/1995 |
| WO | WO 9525503 | 9/1995 |
| WO | WO 9617583 | 6/1996 |

OTHER PUBLICATIONS

Comparison of the mechanical and thermal stability of non–pigmented binaries (English Translation, French Original), 6 pgs.

Comparison of the mechanical and thermal stability of non–pigmented binaries (English Translation, French Original), 7 pgs.

Compartive Studies Relating to D1 (European Patent Application 133 964) (English Translation, French Orignal), 2 pgs.

L'Oréal EP 665 008, Mode Operatoire, Essais binaires (No. 1á7).

Opposition OA 94019 JP, Comparative Tests related to Japanese Opposition (English Translation, French Original), 4 pgs.

Test Results (English Translation, French Original), 4 pgs.

NONY & Associés Cover Letter dated Dec. 21, 2001 and enclosed Test Report.

NONY & Associés Cover Letter dated Feb. 22, 2002 and attached Additional Statement from the Petitioner.

Allied Corporation International NV–SA, *Molecular Weight A–C® Polyethylenes and Copolymers*, by C.J. Auger.

Gelest, Silicone Fluids: Stable, Inert Media, Engineering and Design Properties For: Heat Transfer, Mechanical, Lubrication, Smart Fluid, Dielectric and Optical Applications.

Laboratory Notebook Pages from Inventor Pascal Arnaud (5 pages with English translation attached).

Jul. 25, 2002 Submission to the European Patent Office in Opposition Proceedings for EP 0 665 008 (39 pages with English translation attached).

Claim Amendments Proposed by Patentee During Aug. 6, 2002 Oral Hearing Before the Board of Appeals for EPO 0 665 008 (18 pages with English translation attached).

Fisch de données de Securite, *Dow Corning® 203 Fluid*, date not available.

Paul A. Cadicamo, *Strategy for Lipstick Formulation*, Makeup Documentary/Formulary, *Cosmetic & Toiletries*, vol. 96, Apr. 1981, pp. 55–60.

Fische technique No. 23–363D–02, *Informations sur le Fluide Dow Corning® 203 Agent de démoulage pour les pièces en caoutchouc, en plastique, et les métaux coulés sous pression*, Jan. 1989.

A.C. Dweck, *Lipstick Moulding Techniques—Comparison and Statistical Analysis, Makeup Documentary/Formulary*, vol. 96, Apr. 1981, pp. 61–72, date not available.

Dow Corning®, *Product Information for Dow Corning® 556 Cosmetic–Grade Fluid For Cosmetic and Personal Care Products*, Data Sheet No. 22–242C–01, Aug. 1986.

GE Silicones *SF1023 Silicone Additive for Protective Coatings*, 1992.

Abil Silicones *Abil® AV 20–Abil® AV 1000*, Jul. 1989.

H.F. Fink, *Silicone Surfactants, Part IV*: Silicone Surfactants as Paint Additives, Tenside Surf. Det.* 28 (1991), pp. 306–312.

*OrganoSilicon*, Product Information Data Sheet, Union Carbide Silicone Fluid PC–20.

Adolph Maruszewski, *Steps in Developing a Modern Lipstick, American Perfumer and Cosmetics*, vol. 82, Mar. 1967, pp. 37–40.

Charles Fox, *Gels and Sticks Review and Update, Cosmetics & Toiletries*, vol. 99, Nov. 1984, pp. 19–54.

James J. Slack, *Development of a Modern Lip Gloss with Lanolin Derivatives, American Cosmetics and Perfumery*, vol. 87, Dec. 1972, pp. 41–42.

Steve Goode, *Lip Glosses, Cosmetics and Toiletries*, vol. 92, Jul. 1977, pp. 28–38.

*Coloured Make–up Preparations, Harry's Cosmeticology*, pp. 140–175.

C.D. Vaughan, *Stick Makeup, Cosmetic and Toiletries*, vol. 92, Jul. 1977, pp. 47–53.

G. Van Ham, *Lipstick Formula Variations and Lipstick Properties, Cosmetics and Perfumery*, vol. 90, Jun. 1975, pp. 27–34.

A.L. Fishbach, *Lipsticks—Their Formulation, Manufacuture and Analysis*, Journal of the Society of Cosmetics Chemists*, Presented at the May 14, 1954 Meeting, New York City.

Julio Russ, *Performance Evaluation of Shaded Products*, Makeup Docjmentary/Formulary, *Cosmetics & Toiletries*, vol. 96, Apr. 1981, pp. 25–29.

*Lipstick Packaging, Soap/Cosmetics/Chemical Specialties forr Feb.*, 1988, pp. 62–63.

A.A. Kassem, *Evaluation of Synthetic Oily Materials as Bases for Lipsticks, Cleansing Milks, and Foundation Emulsions, Cosmetics and Perfumery*, vol. 90, Jan. 1975, pp. 31–35.

Mitchell L. Schlossman, *Manufacturing Processes for Color Cosmetics*, Makeup Documentary, *Cosmetics & Toiletries*, vol. 101, Apr. 1986, pp. 95–102.

H. Heinrich, Ph. D., *Stability Tests on Lipsticks, Face Powder, and Make–Up Items**, Presented at the May 18, 1951 Meeting, New York City.

Shirley Ann DeRagon, *Blemish Sticks, Cosmetics and Toiletries*, vol. 92, Jul. 1977, pp. 39–44.

O.K. Jacobi, Ph.D., *Porositones® in Cosmetic Products, American Perfumer and Cosmetics*, vol. 82, Oct. 1967, pp. 83–86.

*Face Powders and Make–Up, Harry's Cosmetics*, pp. 111–139, date not available.

Wendel Dinkel, *Processing of Lipsticks, Cosmetics and Toiletries*, vol. 92, Feb. 1977, pp. 30–34.

Manoel Carames de B.L.F. de Gouvea, *Development of a Lipstick Base, Cosmetics and Toiletries*, vol. 93, Jan. 1978, pp. 15–26.

Geoff Finkenauer, *Lipstick: History as a Window to the Future, Cosmetics & Toiletries*, vol. 101, Apr. 1986, pp. 49–55.

C. Scrofani, *Solid Water–in–Oil Emulsion for Lip Products, Cosmetics & Toiletries*, vol. 108, Jul. 1993, pp. 65–68.

*Cosmetic Stick Comprising Water–in–Oil Emulsion (Brith Patent Specification 1442426), Cosmetics and Toiletries*, vol. 92Jul. 1977, pp. 69–71.

D. Le Botlan, *Determination Du Rapport Solide–Liquid Par Resonance Magnetique Nucleaire Basse Resolution: Etats De L'Eau Dans Une Matiere Grasse Laitiere*, date not available.

*Microcyrstalline Waxes Polywax® Polyethlenes Vybar® Polymers Modified Hydrocarbon Waxes Chemically Reacted Waxes for Product and Process Improvement. New–Product Development. Solutions to Specific Problems in Materials Handling and Characteristics Improvement*, Bareco, date not available.

*Application Data, Makeup Cake*, Release No. BP 100.1, Bareco, Jun. 1982.

*Application Data, Stick Antiperspirant* Release No. 500.15, Bareco, Jan. 1982.

*Product Data, Polywax® Polyethlenes*, Release No. BP100, Nov. 1981.

Synthetic Hydrocarbon Waxes *Industrial Waxes*, pp. 377–382.

*Product Data* Release No. BP100.2, Bareco, Jun. 1982.

*Vybar® 103 & 260, Technical Data* Release No. 500.2, date not available.

*Siltek® L, Technical Data*, Technical Release No. 600.8, date not available.

*Vybar® 825 Polymer, Technical Data*, Technical Release No. 500.3, date not available.

Langer & Co., Properties, Technical Data, Application, Nov. 1992.

*Petrolite® CH–7, CH–12, Development Application Data*, date not available.

Langer & Co. *Lanco–Wax–Guide*, Sep. 1990.

A. Dooms–Goossens, Ph.D., *Contact Sensitivity to Nonoxynols as a Cause of Intolerance to Antiseptic Preparations*, vol. 21, No. 4, Part 1, Oct. 1989.

Langer & Co., *Lanco–BEIT Pigment Concentrates*, Oct. 1989.

Fumiyoshi Yokoyama, *Low Temperature Form of Urea–Polyethylene Complex, Journal of Polymer Science: Polymer Letters Edition*, vol. 19, pp. 91–94 (1981).

Kazuaki Suehiro, *Structural Studies on Molecular Complexes of Polyethers, 1 Urea–Ethylene Oxide Oligomer Complexes, Makromol. Chem.*, 184, pp. 669–674 (1983).

Allied Signal *Actol™ Resin Modifiers, Product Safety Data Sheet*, date not available.

Allied Signal *Actol™ Resin Modifiers, Technical Data for Coatings CTG–013*, A–C Performance Additives, date not available.

Allied Signal *Cover Every Surface Without Cracking, Peeling or Flaking*, A–C Performance Additives, date not available.

A–C Polyethylenes *Gels of Ethylene Copolymer*, date not available.

Allied Chemical *A–C Polyethylenes & Copolymers for Cosmetics, Technical Data*, date not available.

Allied Chemical *A–C Polyethylene in Cosmetic Application, Technical Data*, date not available.
Soap/Cosmetics/Ehcmical Specialities for Feb., 1976 *Polyethylee in Cosmetic Gels*, pp. 56–58.
H. Leszczynska–Bakal, *Physicochemical Properties of Absorptive and Emulsive Ointment Bases with Polyethylene Gel*, Krakow 1970.
Allied Chemical *A–C Polyethylene & Copolymers in Personal Care Products, Technical Data*, date not available.
Allied Chemical, *Creams and Lotions Containing A–C Polyethylene for the Personal Care Industry*, A–C Polyethylene & Copolymers, *Technical Data*, date not available.
Allied Chemical, *A–C Polyethylene 1702, Technical Data Bulletin*, date not available.
Allied Chemical, *Typical Properties of Polymist® Polyethylene Fine Powders*, A–C Polyethlene & Copolymers, *Technical Data*, date not available.
Allied Signal, *Typical Properties/Particle Characteristics for A–C® Polyethylenes, A–C® Copolymers, and Acumist® Micronized Polyethylene Powders*, A–C Polyethylenes, *Technical Data*, Gen 010, date not available.
Allied Corporation, *Ingredients for Success: A–C Polyethylenes and Copolymers for Personal Care Products*, date not available.
Allied Corporation, *Typical Properties of A–C® Polyethylenes and Copolymers*, A–C Polyethylenes, Gen–001, date not available.
Allied Signal, *L'utilisation des A–C® Polyéthylènes et de leurs copolymères en émulsions*, date not available.
Allied Corporation, *Why A–C Polyethylenes and Copolymers?, Typical Advantages of A–C Polyethylenes and Copolymers in Personal Care Products*, Brochure, date not available.
Allied Corporation, *A–C Polyethylenes, Gels of Ethylene Copolymers*, date not available.
Allied Corporation, *A–C Polyethylenes, A–C® Polyethylene & Copolymers as Additives in Antiperspirant Sticks, Technical Data*, date not available.
Allied Signal, *Aclyn® Ionomer Adhesion to Substrates, Aclyn® Low Molecular Weight Ionomers*, date not available.
Allied Signal, *Aclyn® Ionomer Dispersions for Viscosity Control, Aclyn® Low Molecular Weight Ionomers*, date not available.
Allied Signal, *Typical Properties of Aclyn® Low Molecular Weight Ionomers, A–C Polyethylenes*, date not available.
D.F. Danneels, *Low Molecular Weight Ionomers as Processing Aids and Additives*, May 10, 1988, date not available.
Allied Signal, *Acter® 1450 for Polish applications, Technical Data*, Provisional/Experimental, date not available.
Allied Signal, *A–C® Polyethylenes, Personal Care Products Prototype Formulations*, date not available.
Allied Corporation, *Typical Properties of A–C® olyethylenes and Copolymers, Technical Data*, date not available.
*Fabrication With Powdered Polyethylene*, Rubber and Plastics Age, Nov., 1963, pp. 1325–1327.
S. Garry Howell, *Microfine Polyolefin Powders, Technical Section*, SPE Journal, Jun. 1965, pp. 583–586.
Alfred B. Zimmerman, *Powdered Polyethylene Applications and Techniques*, Plastics Technology, vol. 8, No. 7, Jul. 1962, pp. 26–29.
Asao Harashima, *Functions of Silicones and Their Application to Lipsticks*, Special Editing/Current Trends of Reseach and Development of Lip Products, date not available.

Paul Thau, *A New Procedure for the Preparation of Polyethylene–Mineral Oil Gels*, Reprinted from Journal of the Society of Cosmetics Chemists, pp. 359–363 (1965).
I. B. Chang, *Search for the Perfect Gel*, Cosmetics and Toiletries, vol. 92, Jul. 1977.
"Phenyltrimethicone," *International Cosmetic Ingredient Dictionary and Handbook*, Seventh Edition, 1997 vol. 1, p. 1033.
"Synthetic Wax", *CTFA Cosmetic Ingredient Handbook*, Second Edition, p. 439, date not available.
Albin H. Warth, *The Chemistry and Technology of Waxes*, 1947, pp. 7–8.
Allied Chemical, *Typical Properties of A–C Polyethylenes and Copolymers, Technical Data*, G1, date not available.
*Cosmetic Raw Materials Standard*, Revised Edition, Yakuji Nippo Co., 1999, p. 359.
*Technical Data Polywax Polyethylene*, Toyo Petrolite Co., Ltd., date not available.
*Shin Etsu Silicone Oil*, Shin Etsu Chemical Industry Co., date not available.
Noxell Corp.—A Procter & Gamble Co.—Cover Girl—Remarkable Lipcolor SPF 15, date not available.
Chronologix, Line Minimizing Make–Up, Composition, Coty, Dec. 1992.
Vital Perfection—Soin Protecteur Des Levres, Composition, Oct. 1992, Shiseido.
Advanced Performance Lipstick, Composition, Sep. 1993, Shiseido.
Creme Compacte Bronzante SPF 4, Two Way Cake, Composition, May 1993, Shiseido.
SPF 35 Sun Block Stick, Composition, 1993, Shiseido.
*Makeup Sticks, Cosmetics & Toiletries*, vol. 108, Jul. 1993.
Le Crayon Levres (Precision Lip Definer), Composition, Chanel, Jun. 1992.
Shiseido—SPF 35 Sun Block Stick, Water Resistant, *Cosmetic Research* 1993.
Micro Finish—Fond De Teint, Composition, Juvena, Nov. 1992.
Almay Inc.—Luxury Finish Loose Powder, *Cosmetic Research* 1992.
Almay Inc.—Oil Blotting Pressed Powder, *Cosmetic Research* 1992.
New Essentials Ltd.—New Essentials, *Cosmetic Research* 1992.
Pure Finish Loose Powder, *Cosmetic Research*, 1992.
Pure Finish Pressed Powder, *Cosmetic Research*, 1992.
Creme Compacte Bronzante SPF 4, Compositions Shiseido, France, May 1993.
Remarkable Lipcolor, Composition, Cover Girl, Apr. 1992.
Endless Kiss, Composition, Avon, France Feb. 1993.
Creme Lipstick SPF 15, Composition, Cover Girl, Continuous Color, Mar. 1993.
Advanced Performance Lipstick, Composition, Shiseido, Sep. 1993.
Lipstick, Composition, Shiseido, Mar. 1993.
Lip Concentrate, Composition, Almay, Dec. 1991.
Blistex Lip Balm, SPF 10, Composition, Blistex, Jan. 1992.
Vital Defense Lip Treatment, Composition, Vital Defense, Dec. 1991.
Labello Kamille, Composition, Labello, Sep. 1992.
Labello Rose, Composition, Labello, France Sep. 1992.
Labello Sport, Composition, Labello, France, Sep. 1992.
Labello Med, Labello, Composition, France, Sep. 1992.

Chapstick Lip Balm, Cherry, Composition, Chapstick, Dec. 1992.

Chapstick Lip Balm, Medicated, Composition, Chapstick, Jul. 1992.

Chapstick Lip Balm, Composition, Chapstick, Dec. 1992.

Vital Perfection—Soin Protecteur Des Levres, Composition, Shiseido, Oct. 1992.

Rouge Eclat–Rouge A Levres, Composition, Clarins, Mar. 1994.

Rouge Eclat—Brillant A Levres, Composition, Clarins, Mar. 1994.

*Les Tubes Du Siecle, Cosmetic News*, Le Périple, date not available.

*Deutsche Atochem Werke*, Lieferprogramm: Textile Schmelzklebstoffe, date not available.

OrganoSilicon Product Information; *Les Silicones Union Carbide Pour L'Industrie Cosmetique*, 2/91, date not available.

Wacker, Huiles Phényl–Méthylsilicones, Munich, Nov. 1980, pp. 1–11.

Wacker Silicone, Belsil Phenyldimethicone, München, Jan. 1990.

Baysilone–Öle P, Polymere Methylphenylsiloxane, Bayer, pp. 1–10, date not available.

New Product Information, Dow Corning, *Traduction de la fiche tecnique de Toray—Dow Corning*, date not available.

Rouge Á Lévres, date not available.

Historie, *Mémoire de la Beauté*, Parfums, Cosmétiques, Arômes, No. 79—Février–Mars 1988, pp. 93–94.

1960/1969, La Choucroute Et La Banane, *Cosmétique News*, No. Special, 29/06/90.

Historique, De 1890, Les Femmes, *Cosmétique News*, 29/06/90.

*100 Ans De Recherche Cosmetique, Cosmétique* News, Jun. 29, 1990.

*Le Diable Aux Levres, Depeche Mode—Analyse De Presse* Mar. 1994.

Le Dossier Rouge à Lévres, *Les Nouvelles Esthetiques*, Nov. 1984.

Les Nouvelles Esthetiques, *Beauté, souci éternel des femmes*, Fevrier 1985, pp. 69–73.

*Les soins de beauté à la veille de la révolution*, Nouvelles Esthétiques, Apr. 1989, pp. 60–68.

Japanese–language article, Fragrance Journal 1992, pp. 50–56.

Universite De Clermont 1, These pour le Diplôme d'Etat de Docteur en Pharmacie, Les Rouges à Lèvres Preparation et Controles, date not available.

Michael S. Starch, *Silicones in Skin Care Products*, date not available.

*Fats and Waxes, Chemical Abstracts*, vol. 82, 1975, p. 178.

*CA Selects: Water–Based Coatings*, Issue 7, 1993, p. 5.

*CA Selects: Coatings, Inks & Related Products*, Issue 11, 1993, p. 12.

Rhône–Poulenc Développe L'Assistance Technique, In–Cosmetics 93, *Parfumes Cosmétiques Arômes* No. 109, Feb./Mar. 1993.

*Nouveaux Products*, EuroCoat 11, 1993.

CA Selects: Formulation Chemistry, Issue 18, 1990, p. 4.

Goldschmidt Produits Chimiques, Abil B 8853.

Abil® AV 8853, Tego Cosmetics, date not available.

Abil® Silicones, Abil® AV 8853, Tego Cosmetics, date not available.

Huiles De Silicones Diverses, *Silbione Huile 70 641 V 200*, Cosmetologie, May 1985.

Bayer–Silicone, *Baysilone H 250—Additif Pour Peintures et Vernis*, date not available.

Bayer–Silicone, *Baysilone H 160—Additif Pour Peintures et Vernis*, date not available.

Resins & Pigments, *Double Liason—Chimie Des Peintures*, No. 407, Sep. 1989.

*Water–Based Coatings, CA: Selects: Water–Based Coatings*, Issue 20, 1993, p. 1.

Translation of Decision of Opposition Board Regarding Japanese Patent No. 2960658.

Notice of Reasons Japanese Patent was Revoked, pp. 1–29.

Relvon's Reply to L'Oreal's Request for Appeal in Opposition of European Patent Application No. 95400156.6 filed Aug. 8, 2000.

Revlon's Opposition Brief Regarding European Patent Application No. 95400156.6 filed Mar. 11, 1998.

L'Oreal's Initial Response to Revlon's Opposition Brief Regarding European Patent Application No. 95400156.6.

L'Oreal's Supplemental Response to Revlon's Opposition Brief Regarding European Patent Application No. 95400156.6.

Transcript of Oral Proceedings before the European Patent Office dated Aug. 3, 1999 (Original and Translation).

Decision of the European Patent Office Regarding Patent in Application No. 95400156.6 dated Aug. 3, 1999 (Original and English Translation).

L'Oreal's Appeal Brief Regarding European Patent Application No. 95400156.6.

ANHYDROUS COSMETIC OR DERMATOLOGICAL COMPOSITION CONTAINING THE COMBINATION OF A SILICONE OIL AND A WAX MADE FROM AN ETHYLENE HOMOPOLYMER OR COPOLYMER

This application is a continuation of Ser. No. 08/672,082, filed on Jun. 26, 1996, now U.S. Pat. No. 5,750,095, which is a continuation of Ser. No. 08/377,382, filed on Jan. 25, 1995, now U.S. Pat. No. 5,556,613.

The present invention concerns an anhydrous cosmetic or dermatological composition containing, in its fatty phase, the combination of a silicone oil and a wax made from an ethylene homopolymer or copolymer.

The use of silicone oils to formulate products intended for topical application is especially desired, since these oils are harmless and, at the same time, possess a chemical inertia and highly satisfactory lubricating and film-forming properties. In particular, when applied on the skin or keratinic fibers, they produce a film exhibiting simultaneously a homogeneity, a softness, and a gloss that are especially satisfying.

The anhydrous compositions intended for topical application are normally solid or viscous compositions which require, for said application, the presence of waxes, such as natural or paraffin waxes.

However, when the proportions of silicone oil and wax exceed 5% and 3% by weight respectively, poor compatibility has been revealed, with the result that it is possible to obtain a homogeneous mixture after cooling only within markedly limited, predetermined proportion ranges. The term "homogeneous mixture" signifies a mixture in which the various constituents are distributed in identical fashion at all points within the mixture. The lack of constituent compatibility in a given mixture leads to the deterioration thereof, in particular because of the emergence of syneresis. It has been found, moreover, that the problem of compatibility linked to silicone oils arose with respect to the majority of waxes.

Various solutions have been considered to solve this problem. Accordingly, GB 1,140,536 describes waxes containing at least 15% silicone wax. In addition, EP-A-205,961 discloses the use of microcrystalline or hydrocarbon-containing paraffin waxes combined with a resin and a polyolefin. Furthermore, U.S. Pat. No. 5,085,855 describes the use of a combination of a lanolin oil, a lanolin wax, gelling agents, and hydrocarbon-containing polymers. However, according to these diverse solutions, the different constituents must be combined in limited, predetermined proportions, and any addition of a supplementary compound requires the prior preparation of a compatibility diagram which grows increasingly complex as the number of compounds in the composition increases.

After a great amount of research it has now been found, surprisingly and unexpectedly, that, by combining a particular silicone oil and a wax made from an ethylene homopolymer or copolymer, the choice of which was based both on the melting point and on the molecular mass, it was possible to produce silicone oil-based, homogeneous anhydrous cosmetic compositions, without being limited by a restrictive range of proportions.

Therefore, the present invention concerns a silicone oil-based anhydrous cosmetic or dermatological composition having a homogenous fatty phase, characterized by the fact that this fatty phase incorporates a mixture comprising:

(i) at least one silicone oil in a proportion of 5 to 97% by weight of said fatty phase and corresponding to the following formula:

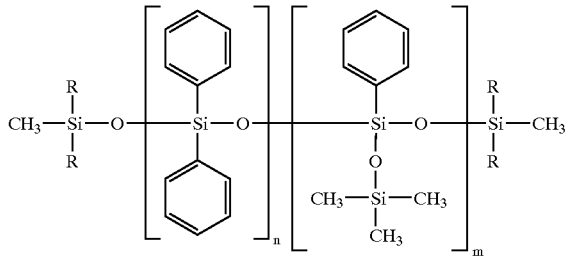

(I)

wherein
R represents alkyl containing 1 to 30 carbon atoms, aryl or aralkyl,
n represents a whole number between 0 and 100, and
m represents a whole number between 0 and 100, provided that the sum n+m is between 1 and 100; and (ii) a wax in a proportion of 3 to 50% of the total weight of said fatty phase, whose melting point is between 50 and 135° C. and which consists of at least one polymer having a molecular weight, as measured by vapor phase osmometry, between 200 and 1,500 selected from ethylene homopolymers and copolymers, and a monomer corresponding to the formula:

$$CH_2=CH-R'\qquad(II)$$

wherein
R' represents alkyl having 1 to 30 carbons, aryl or aralkyl.
Alkyl having 1 to 30 carbons include methyl, ethyl, propyl, isopropyl, decyl, dodecyl, and octadecyl.
Aryl is, preferably, phenyl or tolyl.
The aralkyl is, preferably, benzyl or phenethyl.

Among the silicone oils of formula (I), use is preferably made of those having a viscosity, measured at 25° C., of between 5 and 500 centistokes (cSt).

Among the latter, mention may be made, in particular, of oil commercialized under the trade name "Abil AV 8853" by Goldschmidt, those commercialized under the trade names "DC 556" and "SF 558" by Dow Corning, and that commercialized under the trade name "Silbione 70633 V 30" by Rhone-Poulenc.

"DC 556" is phenyl trimethicone, a compound of formula (1) wherein n is 0 and R is methyl. "Silbione 70633 V 30" is bisphenyl hexamethicone. It is a compound of formula (I) wherein R is methyl, n is 0 and m is 2.

According to a preferred embodiment of the compositions according to the invention, the silicone oil of formula (I) is present in an amount between 10 and 90% by weight of the total weight of the fatty phase.

The use of waxes made from ethylene homopolymers or copolymers, such as those specified above, gives the mixture very numerous advantages. In effect, the mixture produced possesses a high degree of thermal stability, a thixotropy nature yielding excellent spreading properties, a very high degree of water-resistance imparting good cosmetic staying power to products applied to the skin and keratinic fibers. Moreover, these properties make it possible to spread a large quantity of solid particles while preserving good properties of application. In addition, since these products are synthesized, they do not exhibit the variability problems found with natural compounds.

According to a preferred embodiment of the compositions according to the invention, the wax used as previously specified is chosen from among ethylene homopolymers, ethylene-propylene copolymers, and ethylene-hexene copolymers.

The ethylene homopolymers useful according to the invention include, in particular, those sold under the trade names "Polywax 500", "Polywax 655", and "Polywax 1.000" by Bareco, those sold under the trade names "PE 1.500 F" and PEW 1.555" by Langer & Co., those commercialized under the trade name "TN Wax 1.495" sold by R. T. Newey, and "AC 1702" sold by Allied Chemical.

"Polywax 500", "Polywax 655", and "Polywax 1,000" are homopolymers of ethylene having molecular weights of 500, 700, and 1,000, respectively, as determined by vapor pressure osmometry.

Ethylene polymers usable within the scope of the invention include the ethylene-propylene copolymers sold under the trade names "Petrolite CP-7" and "Petrolite CP-12" sold by Bareco, and the ethylene-hexene copolymers sold under the trade names "Petrolite CH-7" and "Petrolite CH-12" by Bareco.

According to a preferred embodiment of the compositions according to the invention, the wax used as described above is present in an amount between 5 and 30% by weight of the total weight of the fatty phase.

The mixture of a silicone oil and a wax made from an ethylene homopolymer or copolymer, as described above, is generally present in the composition according to the invention in a proportion of between 3 and 100% by weight of the total weight of the composition.

In addition to the two constituents of the mixture described above, the fatty phase can also incorporate additives or fatty substances selected from oils and/or waxes. The proportion of additive or fatty substance present in the composition according to the invention is generally between 0.5 and 92% by weight of the total weight of the fatty phase, and preferably between 2 and 85%.

Contrary to known compositions, for which complex compatibility diagrams must be prepared, i.e., diagrams accounting for all of the components of the composition, it suffices merely to prepare, for the compositions according to the invention, a compatibility diagram for the additive in conjunction with one of the compounds in the combination, that is, with the ethylene homopolymer or copolymer wax or with the silicone oil. If the additive is compatible with one of these two components, it is necessarily compatible with the combination thereof.

The oils eventually present in the fatty phase can be of mineral, animal, vegetable, or synthetic origin.

Oils of mineral origin include paraffin oil and vaseline oil. Mineral oils, in general, have a boiling point between 310 and 410° C.

As an animal oil, perhydrosqualene can be cited.

Vegetable oils include, in particular, sweet almond oil, calophyllum oil, palm oil, avocado oil, jojoba oil, sesame oil, olive oil, castor oil and cereal germ oils, e.g., wheat germ oil.

Among the synthetic oils, mention may be made of synthetic esters such as Purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate and diisopropyl adipate.

Other oils useful in the compositions according to the invention include organic alcohols, such as oleic alcohol, linoleic alcohol, linolenic alcohol, isostearyl alcohol and octyldodecanol, and esters derived from lanolic acid, such as isopropyl lanolate and isocetyl lanolate.

Mention may also be made of acetylglycerides, octanoates, and decanoates of alcohols and pol yhydric alcohols, such as those of glycol and glycerol, as well as the ricinoleates of alcohols and polyhydric alcohols, such as those of cetyl.

The waxes potentially present in the fatty phase may be of mineral, fossil, animal, or vegetable origin, or they may be hydrogenated oils or fatty esters solid at 25° C.

The mineral waxes useful according to the invention include microcrystalline, paraffin, vaseline and ceresin waxes.

Fossil waxes include ozokerite and montana wax.

Among animal waxes, mention can be made of beeswax, spermaceti, lanolin wax, and derivatives of lanolin, such as lanolin alcohols, hydrogenated lanolin, hydroxylated lanolin, acetylated lanolin, fatty lanolin acids and acetylated lanolin alcohol.

Vegetable waxes include candellila wax, carnauba wax, Japan wax and cocoa butter.

Hydrogenated oils solidified at 25° C. include hydrogenated ricin oil, hydrogenated palm oil, hydrogenated tallow and hydrogenated coconut oil.

Fatty esters solidified at 25° C. include propylene glycol monomyristate and myristyl myristate.

In addition, the group of waxes comprises cetyl alcohol, stearyl alcohol, mono-, di-, and triglycerides solidified at 25° C., stearic monoethanolamide, colophane and the derivatives thereof, such as glycol and glycerol abietates, sucroglycerides, and calcium, magnesium, zinc, and aluminum oleates, myristates, lanolates, stearates and dihydroxystearates.

The proportion of wax, as specified above, is preferably less than or equal to the proportion of ethylene homopolymers or copolymers.

Furthermore, in the fatty phase of compositions according to the invention oily gel agents can be employed.

These oily gel agents include, in particular, metallic esters, such as polyoxyaluminum stearate and aluminum or magnesium hydroxystearate, cholesterol derivatives and, in particular, hydroxycholesterol, and argillaceous minerals which swell in the presence of oil, and, in particular, those belonging to the montmorillonite group.

According to a special embodiment, the compositions according to the invention may further contain charges, that is, solid compounds in powder form. The proportion of charges in the compositions according to the invention generally ranges between 0.5 and 97% by weight, and preferably between 1 and 40% by weight of the total weight of the composition.

The powdered compounds useful according to the invention may be natural or synthetic, and include, in particular:

a) mineral powders, such as talcum, kaolin, mica, silica, silicates, alumina, zeolites, hydroxyapatite, sericite, titanium dioxide, micatitaniums, zinc oxide, barium sulfate, iron oxides, manganese purple, chrome oxide, cobalt blue, bismuth oxychloride, boron nitride, and metallic powders such as powdered aluminum;

b) vegetable powders, such as cornstarch, wheat, or rice powder;

c) organic powders, such as nylon, polyamide, polyester, polytetrafluoroethylene, or polyethylene powders; and d) organo-metallic powders, such as pigments including zirconium, barium, or aluminum with organic coloring agents.

The powders described above can also be coated, for example using metallic salts of fatty acids, amino acids, lecithin, collagen, silicone-containing compounds, fluorinated compounds, fluorosilicone-containing compounds, or any other conventional coating.

The compositions according to the invention can further comprise a lipophilic additive chosen from among surface active agents, filters, vitamins, hormones, antioxidants, preservatives, dyes, perfumes, and mixtures thereof.

The cosmetic or dermatological compositions according to the invention can exist in various forms, such as oily gels, solid products such as compressed powders or sticks. They can be used, in particular, as skin-care, cleansing or makeup products.

In the case of makeups, these compositions can exist, in particular, as foundations, mascaras, lipsticks, eyeliners or blushers.

The compositions according to the invention are prepared according to conventional methods; that is, by homogenization under heat, then cooling, of the various constituents thereof.

The various composition forms, described above, are obtained based on the nature and proportions of the compounds added thereto, and on the cooling method employed. Thus, by simple cooling with or without stirring, a gel incorporating the composition can be produced. Compositions produced in different forms can also be obtained by pouring the heated mixture in different types of packaging.

Products in compressed form are obviously obtained by exerting pressure on the product.

Illustrative examples of compositions according to the present invention are now given as illustrations.

EXAMPLE 1

Oily Gel

| Phase A: | |
| --- | --- |
| Silicone oil sold under the trade name "SF-558" by Dow Corning | 55 g |
| Sesame oil | 20 g |
| Phase B: | |
| Ethylene homopolymer sold under the trade name "AC 1702" by Allied Chemical Company | 20 g |
| Ethylene homopolymer sold under the trade name "Polywax 655" by Bareco | 5 g |

Phase A was prepared by mixing the constituents thereof while stirring at ambient temperature. After homogenization, the constituents of phase B were added, then the mixture was heated to about 107° C. After melting and homogenization, a clear medium was obtained. The oily gel is then obtained by cooling to ambient temperature.

The gel thus obtained presented excellent spreading properties and formed a very soft and protective film.

EXAMPLE 2

Makeup Foundation

| Phase A: | |
| --- | --- |
| Silicone oil sold under the trade name "DC-556" by Dow Corning | 14 g |
| Hollow microspheres made of a thermoplastic material sold under the trade name "Expancel 551 DE" by Casco-Nobel | 1.5 g |
| Phase B: | |
| Ethylene homopolymer sold under the trade name "PEW 1555" by Langer | 7 g |
| Microcrystalline wax | 4 g |
| Phase C: | |
| 2-hexyl ethyl palmitate | 19 g |
| Hydrogenated isoparaffin | 14 g |
| Isopropyl lanolate | 9.3 g |
| Propyl paraben | 0.2 g |
| Phase D: | |
| Iron oxides | 3 g |
| Titanium dioxide | 13 g |
| Zinc oxide | 3 g |
| Talcum | 12 g |

The constituents of phases B and C were mixed, then heated to approximately 107° C. After melting all of the constituents, the mixture was homogenized, then cooled to a temperature of approximately 90° C. Phase A, whose constituents have been preliminarily mixed at ambient temperature, and, finally, the constituents of phase D were added in succession. After homogenization, the mixture thus obtained was poured under heat into cupels.

After cooling at ambient temperature, a makeup foundation was obtained which possessed excellent skin-spreading properties and very good staying power.

EXAMPLE 3

Lipstick

| Phase A: | |
| --- | --- |
| Silicone oil sold under the trade name "DC-556" by Dow Corning | 23 g |
| Phase B: | |
| Ethylene homopolymer sold under the trade name "PEW 1555" by Langer | 7 g |
| Microcrystalline wax | 7 g |
| Lanolin | 7 g |
| Phase C: | |
| Ricin oil | 22 g |
| Sesame oil | 22 g |
| Phase D: | |
| Pigments | 12 g |

The constituents of phases B and C were mixed by heating at approximately 107° C. After the waxes were melted, the mixture was homogenized, then cooled to approximately 95° C. Phase A, then phase D were added in succession. After homogenizing the mixture, the latter was poured into stick-shaped compartments.

After cooling, a lipstick was obtained which was applied quite easily to the lips and had a very high degree of softness. Moreover, it stayed in place well; that is, it showed excellent resistance and did not run.

EXAMPLE 4

Lipstick

| Phase A: | |
|---|---|
| Silicone oil sold under the trade name "Silbione 70633 V 30" by Rhone-Poulenc | 10 g |
| Jojoba oil | 25 g |
| Sesame oil | 27 g |
| Phase B: | |
| Ethylene homopolymer sold under the trade name "Polywax 500" by Bareco | 20 g |
| Lanolin | 6.5 g |
| Phase C: | |
| Pigments | 11.5 g |

EXAMPLE 5

Lipstick

| Phase A: | |
|---|---|
| Silicone oil sold under the trade name "Silbione 70633 V 30" by Rhone-Poulenc | 10 g |
| Jojoba oil | 25 g |
| Sesame oil | 27 g |
| Phase B: | |
| Ethylene copolymer and propylene sold under the trade name "Petrolite CP-7" by Bareco | 20 g |
| Lanolin | 6.5 g |
| Phase C: | |
| Pigments | 11.5 g |

The lipsticks in Examples 4 and 5 are prepared in a manner similar to that of Example 3.

What is claimed is:

1. A silicone oil-based anhydrous cosmetic or dermatological composition comprising a homogeneous fatty phase, said fatty phase comprising a mixture of:

(i) at least one silicone oil, in an amount ranging from 5 to 97% of the total weight of said fatty phase, having the formula:

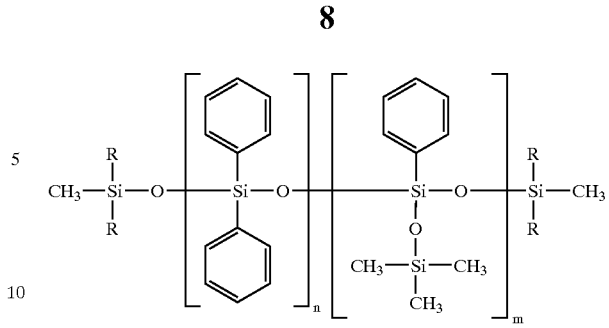

wherein:
R represents alkyl having 1 to 30 carbon atoms, aryl or aralkyl,
n represents a whole number between 0 to 100, and
m represents a whole number between 0 and 100, provided that the sum of n+m is between 1 and 100; and (ii) a wax in an amount ranging from 3 to 50% by weight based on the total weight of said fatty phase, having a melting point between 50 and 135 C, said wax being a homopolymer or copolymer having a molecular weight between 200 and 700 and being selected from the group consisting of ethylene homopolymers and copolymers of ethylene with a monomer having the formula:

$$CH_2=CH-R'$$ (II)

wherein:
R' represents alkyl having 1 to 30 carbon atoms or aryl.

2. A composition as recited in claim 1, wherein the at least one silicone oil is present in an amount ranging from about 10% to about 90% by weight with respect to the total weight of the fatty phase.

3. A composition as recited in claim 1, wherein the wax is present in an amount ranging from about 5% to about 30% by weight with respect to the total weight of the fatty phase.

4. A composition as recited in claim 1, wherein the at least one silicone oil has a viscosity of 5 to 500 centistokes measured at 25° C.

5. A composition as recited in claim 1, wherein the at least one silicone oil is selected from the group consisting of phenyl trimethicone and bisphenyl hexamethicone.

6. A composition as recited in claim 5, wherein the at least one silicone oil is phenyl trimethicone.

7. A composition as recited in claim 5, wherein the at least one silicone oil is bisphenyl hexamethicone.

8. A composition as recited in claim 1, wherein the molecular weight of the wax is between 200 and 500.

9. A composition as recited in claim 8, wherein the at least one silicone oil is selected from the group consisting of phenyl trimethicone and bisphenyl hexamethicone.

10. A composition as recited in claim 9, wherein the at least one silicone oil is phenyl trimethicone.

11. A composition as recited in claim 9, wherein the at least one silicone oil is bisphenyl hexamethicone.

12. A composition as recited in claim 1, wherein the wax is an ethylene homopolymer.

13. A composition as recited in claim 12, wherein the at least one silicone oil is selected from the group consisting of phenyl trimethicone and bisphenyl hexamethicone.

14. A composition as recited in claim 13, wherein the at least one silicone oil is phenyl trimethicone.

15. A composition as recited in claim 13, wherein the at least one silicone oil is bisphenyl hexamethicone.

16. A composition as recited in claim 12, wherein the molecular weight of the ethylene homopolymer is between 200 and 500.

17. A composition as recited in claim 16, wherein the at least one silicone oil is selected from the group consisting of phenyl trimethicone and bisphenyl hexamethicone.

18. A composition as recited in claim 17, wherein the at least one silicone oil is phenyl trimethicone.

19. A composition as recited in claim 17, wherein the at least one silicone oil is bisphenyl hexamethicone.

20. A composition as recited in claim 12, wherein the molecular weight of the ethylene homopolymer is between 500 and 700.

21. A composition as recited in claim 20, wherein the at least one silicone oil is selected from the group consisting of phenyl trimethicone and bisphenyl hexatnethicone.

22. A composition as recited in claim 21, wherein the at least one silicone oil is phenyl trimethicone.

23. A composition as recited in claim 21, wherein the at least one silicone oil is bisphenyl hexamethicone.

24. A composition as recited in claim 1, wherein said fatty phase further comprises a fatty substance.

25. A composition as recited in claim 24, wherein said fatty substance is present in an amount ranging from 0.5 to 92% by weight based on the total weight of said fatty phase.

26. A composition as recited in claim 1, further comprising a vegetable wax.

27. A composition as recited in claim 26, wherein said vegetable wax is carnauba wax.

28. A composition as recited in claim 1, further comprising a mineral wax.

29. A composition as recited in claim 28, wherein the mineral wax is ceresin wax or microcrystalline wax.

30. A composition as recited in claim 1, further comprising a fossil wax.

31. A composition as recited in claim 30, wherein the fossil wax is ozokerite.

32. A composition as recited in claim 1, further comprising an animal wax.

33. A composition as recited in claim 32, wherein the animal wax is selected from the group consisting of beeswax and spermaceti.

34. A composition as recited in claim 32, wherein the animal wax is selected from the group consisting of lanolin wax, lanolin alcohol, hydrogenated lanolin, hydroxylated lanolin, acetylated lanolin, fatty lanolin acids and acetylated lanolin alcohol.

35. A composition as recited in claim 1, further comprising a hydrogenated oil which is solid at 25 C.

36. A composition as recited in claim 1, further comprising a fatty ester which is solid at 25 C.

37. A composition as recited in claim 1, further comprising magnesium myristate.

38. A composition as recited in claim 1, further comprising a vegetable oil.

39. A composition as recited in claim 38, wherein the vegetable oil is jojoba oil.

40. A composition as recited in claim 1, further comprising a synthetic oil.

41. A composition as recited in claim 1, further comprising an animal oil.

42. A composition as recited in claim 1, further comprising an organic alcohol.

43. A composition as recited in claim 42, wherein the organic alcohol is linolenic alcohol.

44. A composition as recited in claim 1, further comprising an organic powder.

45. A composition as recited in claim 44, wherein the organic powder is a polyamide.

46. A composition as recited in claim 44, wherein the organic powder is polytetrafluoroethylene.

47. A composition as recited in claim 1, further comprising a mineral powder.

48. A composition as recited in claim 47, wherein the mineral powder is barium sulfate.

49. A composition as recited in claim 47, wherein the mineral powder is titanium dioxide.

50. A composition as recited in claim 47, wherein the mineral powder is talcum.

51. A composition as recited in claim 47, wherein the mineral powder is silica.

52. A composition as recited in claim 47, wherein the mineral powder is a silicate.

53. A composition as recited in claim 47, wherein the mineral powder is alumina.

54. A composition as recited in claim 47, wherein the mineral powder is a zeolite.

55. A composition as recited in claim 47, wherein the mineral powder is zinc oxide.

56. A composition as recited in claim 47, wherein the mineral powder is iron oxide.

57. A composition as recited in claim 47, wherein the mineral powder is mica.

58. A composition as recited in claim 1, further comprising an organo-metallic powder.

59. A composition as recited in claim 58, wherein the organo-metallic powder is a pigment.

60. A composition as recited in claim 59, wherein the organo-metallic powder is a pigment selected from the group consisting of zirconium with organic coloring agents, barium with organic coloring agents and aluminum with organic coloring agents.

61. A composition as recited in claim 1, further comprising a pigment.

62. A composition as recited in claim 1, further comprising an oily gel agent.

63. A composition as recited in claim 62, wherein the oily gel agent is a cholesterol compound.

64. A composition as recited in claim 62, wherein the oily gel agent is an argillaceous mineral.

65. A composition as recited in claim 64, wherein the argillaceous mineral is a montmorillonite.

66. A composition as recited in claim 1, further comprising an antioxidant.

67. A composition as recited in claim 1, further comprising a preservative.

68. A composition as recited in claim 1, further comprising a filter.

69. A composition as recited in claim 1, further comprising a vitamin.

70. A composition as recited in claim 1, wherein the composition is a solid product.

71. A composition as recited in claim 70, wherein the solid product is a stick.

72. A composition as recited in claim 71, wherein the solid product is a lipstick.

73. A composition as recited in claim 70, wherein the solid product is a compressed powder.

74. A composition as recited in claim 1, wherein the composition is a make-up composition.

75. A composition as recited in claim 74, wherein the make-up composition is a foundation.

76. A composition as recited in claim 74, wherein the make-up composition is a blusher.

77. A composition as recited in claim 18, wherein the composition is a solid product.

78. A composition as recited in claim 77, wherein the solid product is a stick.

79. A composition as recited in claim 78, wherein the solid product is a lipstick.

80. A composition as recited in claim 77, wherein the solid product is a compressed powder.

81. A composition as recited in claim 18, wherein the composition is a make-up composition.

82. A composition as recited in claim 81, wherein the make-up composition is a foundation.

83. A composition as recited in claim 81, wherein the make-up composition is a blusher.

84. A composition as recited in claim 22, wherein the composition is a solid product.

85. A composition as recited in claim 84, wherein the solid product is a stick.

86. A composition as recited in claim 85, wherein the solid product is a lipstick.

87. A composition as recited in claim 84, wherein the solid product is a compressed powder.

88. A composition as recited in claim 22, wherein the composition is a make-up composition.

89. A composition as recited in claim 88, wherein the make-up composition is a foundation.

90. A composition as recited in claim 88, wherein the make-up composition is a blusher.

* * * * *

UNITED STATES PATENT AND TRADEMARK OFFICE
CERTIFICATE OF CORRECTION

PATENT NO.   : 6,843,982 B1
DATED        : January 18, 2005
INVENTOR(S)  : Pascal Arnaud et al.

It is certified that error appears in the above-identified patent and that said Letters Patent is hereby corrected as shown below:

<u>Column 9,</u>
Line 13, "hexatnethicone" should read -- hexamethicone --.

Signed and Sealed this

Twenty-sixth Day of April, 2005

JON W. DUDAS
*Director of the United States Patent and Trademark Office*